(12) United States Patent
Winters

(10) Patent No.: US 7,234,473 B1
(45) Date of Patent: Jun. 26, 2007

(54) DENTAL FLOSS DISPENSERS, FLOSSING TOOLS, AND TOOTHBRUSH FLOSSER

(76) Inventor: Steven Nebeker Winters, 2605 Commonwealth Ave., Salt Lake City, UT (US) 84109

( * ) Notice: Subject to any disclaimer, the term of this patent is extended or adjusted under 35 U.S.C. 154(b) by 216 days.

(21) Appl. No.: 10/980,431

(22) Filed: Nov. 2, 2004

Related U.S. Application Data

(63) Continuation-in-part of application No. 10/194,661, filed on Jul. 12, 2002, now abandoned, which is a continuation of application No. 09/323,877, filed on Jun. 1, 1999, now abandoned.

(60) Provisional application No. 60/087,518, filed on Jun. 1, 1998.

(51) Int. Cl.
*A45D 44/18* (2006.01)

(52) U.S. Cl. ...................................... 132/309; 132/325

(58) Field of Classification Search ................ 132/323, 132/324, 325, 326, 327, 328, 308, 309; 15/167.1; D4/104, 108, 113
See application file for complete search history.

(56) References Cited

U.S. PATENT DOCUMENTS

| | | | |
|---|---|---|---|
| 893,345 A | 7/1908 | Monson |
| 1,475,789 A | 11/1923 | Buckley |
| 1,640,607 A | 8/1927 | Kitley |
| 1,890,788 A | 12/1932 | Landis |
| 1,958,505 A | 5/1934 | Aki |
| 2,517,806 A | 8/1950 | Streiler |
| 2,754,833 A | 7/1956 | Vecchio |
| 3,480,190 A | 11/1969 | Freedman |
| 3,718,146 A | 2/1973 | Myers |
| 3,890,986 A | 6/1975 | Gerlich |
| 3,901,251 A | 8/1975 | Johnston |
| 4,342,324 A | 8/1982 | Sanderson |
| 4,495,957 A | 1/1985 | Beggs et al. |
| 4,622,986 A | 11/1986 | Harris et al. |
| 4,657,034 A | 4/1987 | Koski |
| 4,788,990 A | 12/1988 | Wisegerber |
| 4,844,104 A | 7/1989 | Martin |
| 4,920,993 A | 5/1990 | Mackie |

(Continued)

*Primary Examiner*—Todd E. Manahan
(74) *Attorney, Agent, or Firm*—Thorpe North & Western, LLP

(57) ABSTRACT

A dental floss dispenser having a shape or attaching elements which allows it to be held during flossing. One embodiment has a finger spool which is worn on the finger tip or finger during flossing. The dental floss dispenser may also incorporate a finger grip so that the dispenser can be held by the lower fingers, a contoured shape to better fit the hand of the user, a wide or weighted base for easy pick-up, or a U-shaped indentation for quickly grabbing dental floss at the commencement of flossing. A take up spool is designed to be used during the flossing procedure as an anchor for the dental floss to thereby allow the user to floss without wrapping floss around a take up finger or fingers. The take up spool is incorporated into the handle of a toothbrush. By using the dispenser or the take up spool in the flossing procedure, time is saved and flossing becomes more convenient and efficient. The take up spool includes a plurality of tapered notches, each tapered notch having an associated holding slot, each tapered notch for guiding a previously unattached end portion of a length of dental floss into the associated holding slot and securing the dental floss therein to securely hold and manipulate one end of the length of dental floss during the flossing process.

17 Claims, 12 Drawing Sheets

U.S. PATENT DOCUMENTS

| | | |
|---|---|---|
| 4,926,820 A | 5/1990 | Wearn |
| 4,934,389 A | 6/1990 | Pettiford |
| D313,875 S | 1/1991 | Chen |
| 5,199,452 A | 4/1993 | Cheng |
| 5,232,002 A | 8/1993 | McClallen |
| D358,001 S | 5/1995 | Ramsey |
| 5,477,871 A | 12/1995 | Sanchez, Jr. |
| 5,503,168 A | 4/1996 | Wang |
| 5,570,710 A | 11/1996 | Wei et al. |
| 5,573,022 A | 11/1996 | Winters |
| 5,617,884 A | 4/1997 | Allison |
| 5,678,578 A | 10/1997 | Kossak et al. |
| 5,680,875 A | 10/1997 | Winters |
| 5,692,532 A | 12/1997 | Gabrovsek |
| 5,718,252 A | 2/1998 | Wei et al. |
| 5,842,490 A | 12/1998 | Jensen |
| 5,865,195 A | 2/1999 | Carter |
| 5,878,759 A | 3/1999 | Arias |
| 6,065,480 A | 5/2000 | Mader |

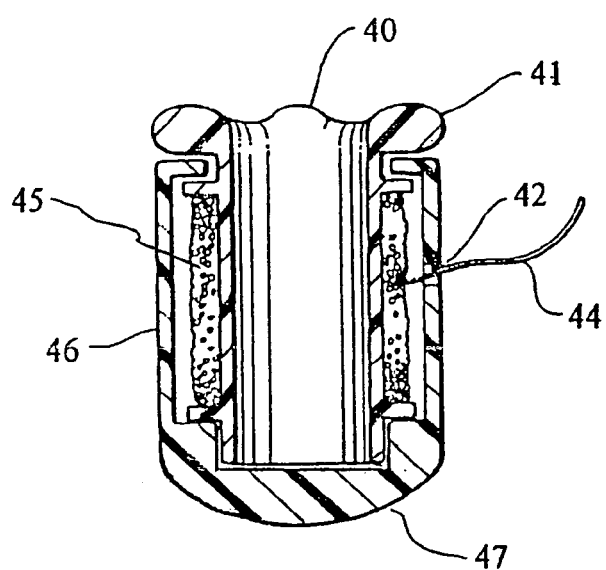
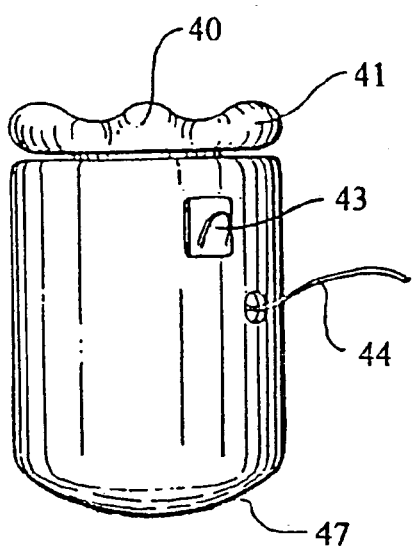
FIG. 12
FIG. 13
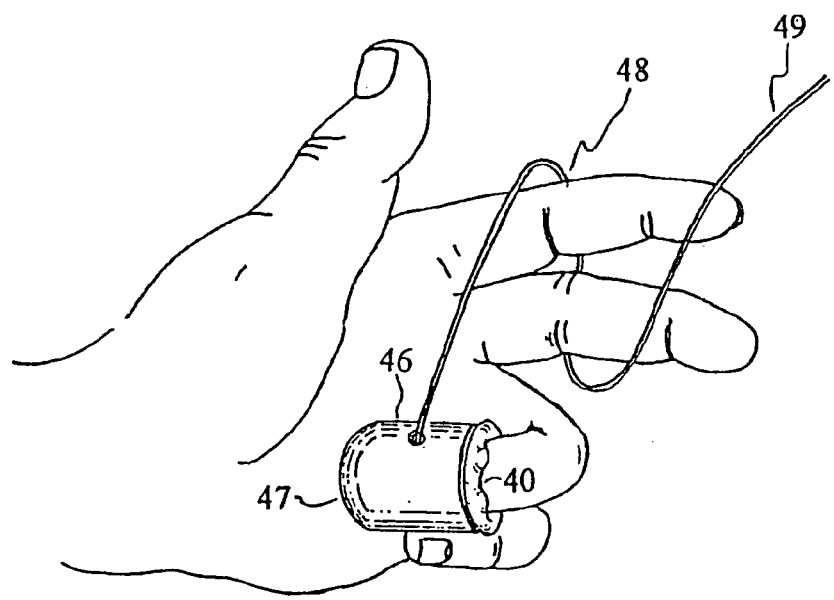
FIG. 14

DENTAL FLOSS DISPENSERS, FLOSSING TOOLS, AND TOOTHBRUSH FLOSSER

RELATED APPLICATIONS

This is a continuation-in-part of copending application Ser. No. 10/194,661 filed Jul. 12, 2002 now abandoned, entitled "Dental Floss Dispensers, Flossing Tools and Toothbrush Flosser," which was a continuation of application Ser. No. 09/323,877, filed Jun. 1, 1999 now abandoned, entitled "Dental Floss Dispensers, Flossing Tools and Toothbrush Flosser," which claimed priority based on provisional Patent Application No. 60/087,518, entitled "Dental Floss Dispensers and Flossing Tools," filed on Jun. 1, 1998 by Steven Nebeker Winters, Timothy S. Evans, and Brent A. Larson.

BACKGROUND OF THE INVENTION

1. The Field of the Invention

The present invention relates to tools, assemblies, and apparatus that aid in the dental flossing process and more particularly to those tools or devices that require the use of both hands to operate while leaving the thumb and forefingers free to guide the floss between the teeth or to wipe or brush tooth surfaces. This category of device uses the fingers of the person applying the dental floss to guide and provide the "brushing" action of the dental floss.

Specifically, the present invention treats novel dispensers of dental floss where the floss is incrementally dispensed and the rate of dispensing is controlled by one hand, or by a finger or fingers of that hand. Furthermore, once dispensed, the floss is not cut from the dispenser but held in place with respect to the dispenser, so that the dispenser itself becomes part of the flossing process. The present invention also treats novel ways to take up floss as it is used, or soiled.

2. Present State of the Art

Daily flossing has been proven to be an effective and preferred method of oral hygiene when combined with brushing after meals. Some of the benefits that accrue from flossing are healthy teeth and gums, and prevention of tooth decay. Research now indicates that persons who floss may actually live longer and prevent some types of heart and arterial damage.

Dentists continuously and vigorously endorse flossing as an integral part of oral hygiene; yet, there continues to be resistance by the public to floss on a regular basis. The process of flossing requires that a strand of dental floss be considerably tensioned and then forced between the teeth. The tensioned floss is then rubbed along the sides of the teeth beneath the gum line thereby using friction to remove plaque. Additionally, food particles and other debris are quickly and easily removed by this action.

Flossing can be done without the aid of tools. This is accomplished by taking a length of dental floss and wrapping the floss around fingers on both hands leaving approximately two to four inches between the hands. With the floss thus wrapped, a person may tension the dental floss by pulling the hands apart. Using the thumbs and the index, or middle fingers, the user may guide the floss in between the teeth. If teeth are tightly packed together, a fair amount of force is necessary to drive the floss in between them.

The forces of keeping the floss tensioned and driving the floss between the teeth tends to cause uncomfortable or painful tightening on to the fingers around which the floss is wrapped. A user may even find it necessary to interrupt the flossing process entirely in order to loosen the floss from around the fingers to relieve pressure or restore blood flow.

Another common problem is excess waste of dental floss. When wrapping floss around the fingers, a certain excess amount must be used in order to provide enough coils so that the floss will not slip off when tensioned.

Dentists and dental hygienists encourage patients to use a fresh segment of floss in between each new pair of teeth to avoid transferring bacteria from gap to gap. A common problem which is encountered with most dental flossing tools is the awkward nature of advancing the floss so that fresh, unsoiled floss can be used. A fair amount of disruption occurs when floss is advanced from one hand to the other and then retensioned thus making the floss ready for continued flossing. The overall effect is to increase flossing time, waste floss because of lack of control in how much floss gets advanced, and frustrate the user due to general inconvenience.

Various devices and assemblies have been proposed to overcome these problems of flossing. While all of them are effective at reducing the pain involved with winding the floss around the fingers, they have varying degrees of success dealing with the other above-mentioned problems. Furthermore, many are not designed to dispense floss and remain connected to the dental floss to assist in the flossing process itself. These devices include U.S. Pat. No. 3,393,687 to Whitman, U.S. Pat. No. 4,403,625 to Sanders, U.S. Pat. No. 3,696,821 to Adams, U.S. Pat. No. 4,050,470 to Miller, U.S. Pat. No. 5,564,446 to Wiltshire, U.S. Pat. No. 5,638,841 to Levine, and U.S. Pat. No. 5,692,532 to Gabrovsek.

The Whitman applicator provides for one end of the floss to be connected to the applicator while the other end is held by the hand not holding the applicator. Though this applicator effectively may solve the problem of finger pain, it requires a fair amount of effort to thread and set it up for use. Furthermore, the free end of the floss may have to be wrapped or coiled around the finger in order to allow proper tensioning and guidance. Moreover, it does not allow the user to incrementally move the floss strand to get fresh floss without the burdensome process of unthreading and cutting the existing floss strand and then rethreading the applicator with a new strand of floss. Additionally, another supply of dental floss is needed.

Sanders discloses a disposable hygienic device that acts both as a toothpick as well as a flossing tool. The problem of the pain in the index fingers due to the wrapped floss is solved, but there is no provision for using a continuous strand of floss since the Sanders device is disposable; it is not designed to accommodate new strands of floss. It further fails to incrementally use the floss in a manner that leaves no wasted floss. The effective area of usable floss is relatively small and is likely to become extremely soiled. It also appears that the two pieces that form the handles or the grasping means of the device are very small thereby making it somewhat difficult to grasp. Again, there is no sizeable supply of floss that can be used.

Adams discloses a pair of thimble like devices to fit over the tops of the index fingers. This allows control and proper tensioning of the floss while protecting the index fingers from painful floss winding. However, moving to a fresh piece of floss is an awkward proposition since one must loosen the thimbles in order to move the floss. Furthermore, the amount of tension created by this method may be less than optimal. It would likewise be wasteful, since users would likely prefer to pull enough floss between the thimbles so that soiled floss is not in contact with the fingers. Yet again, another supply source is needed to dispense the floss.

Miller discloses an assembly that is used like the present invention with the exception of fresh floss advancement. Finger pain is eliminated but moving the strand of floss in order to place a fresh, unsoiled piece of floss next to the tooth requires disconnecting one of the two members and reconnecting it elsewhere. This is a clumsy process that would be time consuming and wasteful of floss. As with the other disclosures, a completely difference source for the floss is required.

Wiltshire discloses a floss strand between a pair of handles which are sufficiently long so that they can be inserted inside the user's mouth. For carefully guiding floss between teeth a person's own fingers will always be more dexterous than a long handle.

Levine discloses a device which has a handle portion and a finger like portion. Floss is threaded through a hole at the tip of the finger like portion of the device. Again the device is inserted into the mouth. The more dexterous fingers are not used to manipulate the floss in between the teeth.

Gabrovsek discloses a two-piece device. One piece has an internal spool of floss as well as a finger-like element which is inserted into the mouth. The other piece also has a finger-like element which is inserted into the mouth during flossing. Once again the more dexterous fingers are not used to guide the floss.

None of the previous devices effectively solve the problem in the art of easily transporting a strand of floss such that fresh unsoiled floss can be placed for use in between each new pair of teeth. The various ways of repositioning fresh floss in the above-mentioned patents are all unwieldy and hinders the task of flossing the teeth. Furthermore, most of them do not conveniently store a large quantity of dental floss or conveniently supply the floss as needed. This in turn makes the chore of daily flossing an oppressive and time consuming operation.

In addition, many of the above-mentioned ways of advancing the floss tend to be relatively wasteful of the floss. Most leave significant quantities of the floss in a clean and unused condition. The awkwardness of the advancement mechanisms tends to affect the user negatively in that she will tend to continually floss with soiled floss rather than go to the trouble of advancing the floss to get an unsoiled portion of the floss in contact with the teeth thus compromising the quality and effectiveness of the flossing operation.

The inventions previously disclosed by Winters, U.S. Pat. Nos. 5,573,002 and 5,680,875 have addressed these issues. However, various devices and assemblies have now been proposed to overcome additional flossing issues.

SUMMARY AND OBJECTS OF THE INVENTION

It is an object of this invention to provide a device and method for more conveniently taking up used and soiled floss during the flossing process. The hand held take up spool member may have raised edges or protrusions along with indentations or depressions designed to facilitate rotating of the member. Edges or protrusions may be pronounced or dull and rounded. The member may have a textured surface to improve user's grip and ability to rotate the member.

It is another object of this invention to provide a hand held take up spool member which rotates in an attached housing. Rotating can be accomplished by squeezing and releasing a handle on the housing. A small motor could also be used to rotate the spool within the housing.

It is another object of this invention to provide a hand held take up member which advance the used portion of floss by directly rolling a wheel or spool with a thumb or finger. The used floss may be rolled past the wheel or spool or the used floss may be rolled on to the wheel or spool.

It is another object of this invention to incorporated the take up element into the handle of a toothbrush reducing the number of tools needed for brushing and flossing from two items to one. Also the user will have an attachment reminder during brushing that flossing also needs to be done daily. The take up element, such as the toothbrush handle, may include a plurality of tapered notches, each tapered notch having an associated holding slot, each tapered notch for guiding a previously unattached end portion of a length of dental floss into the associated holding slot and securing the dental floss therein. The take up element may be the type that is completely rotated in the hand or it may be the type with the wheel or spool which is rotated by the user's finger or thumb.

It is another object of this invention to provide a floss dispenser that can be comfortably and conveniently held while flossing but does not require a floss strand or floss spool locking mechanism thus providing another method for effective, convenient, and efficient flossing. The subsequent reduction in moving parts will decrease the cost of manufacturing and assembly. The dispenser may have an attached element that may be secured by one or more fingers. This attached element may be ring shaped and a finger could be placed through it to secure the dispenser during flossing. The dispenser may also be secure by a variety of non-ring shaped elements through which a finger or fingers could be place or which could be gripped by a finger or fingers during flossing. For dispensers which have a ring shaped or non-ring shaped element which is secured with a finger or fingers, the dispenser would not have held inside the hand. The dispenser could be secured during flossing such that it was essentially suspended below the hand.

Because there is no locking mechanism the floss strand may be secured during flossing by wrapping it around a finger or fingers or by weaving it around and through a few fingers. If the fingers are held tightly together the floss can be prevented from slipping between and around them. When a fresh new segment of floss is needed the fingers can be slightly spread apart or generally relaxed allowing the floss to slip between and around them. This method allows the floss to be incrementally advanced during flossing.

It is another object of this invention to provide a dispenser in the form of a spool of dental floss which is worn around a finger or on a finger tip. The unused floss on the spool is protected by a revolving sleeve or by a removable and replaceable cover. If the spool is worn around the finger, bending the finger may be used to restrain the rotation of the spool thus allowing the floss to be sufficiently tensioned for flossing. If the spool is worn on the finger tip, pressing the finger tip and the flosser into the palm of the hand, as well as bending the finger, may be used to restrain the rotation of the spool.

Furthermore, the floss source is preferably a dispenser that is specifically designed to fit sufficiently matingly in the palm of the hand during flossing. This is the preferred designed. Because the dispenser does not have a locking mechanism for the floss strand or floss spool, the floss may be tensioned by wrapping it around, or by weaving it between fingers. Various different means may be used to accomplish the tensioning of the floss. A number of such means will be explained and others will be apparent to those skilled in the art.

All of the above designs free the more dexterous fingers and allow them to be used only for manipulating the floss strand between the teeth while the less dexterous lower fingers are mainly employed for alternately advancing and tensioning the floss strand. Flossing time is greatly reduced because the device allows each finger to be utilized for the task for which it is most suited.

The preferred floss dispenser doubles as a tool to aid in flossing and the floss stays connected to the dispenser until after flossing is completed. This tool aspect of the dispenser provides substantial benefit to the user regardless of whether a take-up member is used or whether "take-up" is accomplished in the conventional manner using finger on the hand opposite of the one holding the dispenser/tool.

Another important object of the invention is to provide an easy way of advancing the strand of floss. The rotational scheme used whereby floss is rotated from a source dispenser onto a take-up spool is easily accomplished with the fingertips. The cross-section of the take-up spool can be round or have three or more sides. A squared cross-section with pronounced edges and indentations between edges is one of many designs which can be easily rotated in the hand using the fingers. This method does not necessitate any cumbersome repositioning of the devices or movement of the hands. In this way, total floss time can be shortened and the entire process can be made more enjoyable.

It is a further object of this invention to reduce dental floss waste. Since floss is not wrapped around any fingers, it is unnecessary to cut off more floss than will be used simply to get the proper tensioning for the flossing process. Secondly, the rotational scheme allows the floss to be advanced incrementally thereby efficiently utilizing nearly the entire quantity of the floss by placing it in direct contact with the teeth to be cleaned at one time or another. Thirdly, the floss can be advanced by an increment equal to the side width of a take up spool. If the take-up spool has sides which are a half inch in width, a quarter turn of the take up spool will only advance the floss a half inch. When floss is directly wrapped around the finger, the only possible advancement length is the circumference of the finger, which for adults can be one and one half inches up to two and one half inches. Being forced to advance by such long increments causes a lot of the floss to be unusable.

Yet another object of this invention is to allow the user greater flexibility in choosing the length of working floss. Through being able to increase or decrease the length of working floss by finer increments, the user can continuously alter the length to change the working length and maintain the most comfortable working length while working from the back of the mouth which generally requires longer lengths to the front which requires shorter lengths.

A further object of this invention is improved flossing of the teeth. This is accomplished by allowing more new and unused floss to be subjected to the tooth surface. Fresh, unsoiled floss is a more effective cleaning tool and it is less likely to transfer bacteria from gap to gap.

A further object of this invention is to reduce the amount of time required for flossing. By using the hand held dispenser and the finger spool, the time required for wrapping the floss around a finger is eliminated. As soon as the dispenser is placed in the hand and the floss is inserted in the notch or around the protruding knob on the take-up spool and the take-up spool is rotated once or twice, the individual is ready to begin flossing. This preparation can be accomplished in less time than the standard process which entails removing the floss from a dispenser, cutting it then wrapping it around one finger on each hand.

Yet a further object of the invention is to eliminate the pain associated with flossing caused by tightly winding dental floss around a fingers. Since the means of support for the tensioning can be the floss dispenser and take-up members, stress on the fingers is reduced. Even if the floss dispenser is used with a finger to take up used floss, the pain in even that one finger can be reduced by pulling mostly with the dispenser to work the floss between tight tooth connections.

These and other objects and features of the present invention will become more fully apparent from the following description and appended claims, or may be learned by the practice of the invention as set forth hereinafter.

While relatively specific embodiments of the rotational dental floss holder and assembly are disclosed with the accompanying drawings, it will be understood that variations and other assemblies will occur to those skilled in the art.

Additional objects and advantages of the invention will be set forth in the description which follows, and in part will be obvious from the description, or maybe learned by the practice of the invention. The objects and advantages of the invention maybe realized and obtained by means of the instruments and combinations particularly pointed out in the appended claims.

To achieve the foregoing objects, and in accordance with the invention as embodied and broadly described herein an improved dental floss dispenser adapted to aid in the flossing process is provided.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 12 shows a cutaway view of another embodiment of a dental floss dispenser with a freely rotating sleeve covering the floss. The spool rotates on the finger while the sleeve is held in place by the taut strand of floss which extrudes from the hole.

FIG. 13 shows a non-cutaway view of the dispenser of FIG. 12 having a freely rotating sleeve.

FIG. 14 shows a non-cutaway view of the dispenser of FIG. 12 on the finger tip of a user. Pressing the spool into the palm of the hand or wrapping the floss strand around available fingers are some of methods which can be used to tension the floss strand during flossing.

DETAILED DESCRIPTION OF THE PREFERRED EMBODIMENTS

Figures 1, 2:
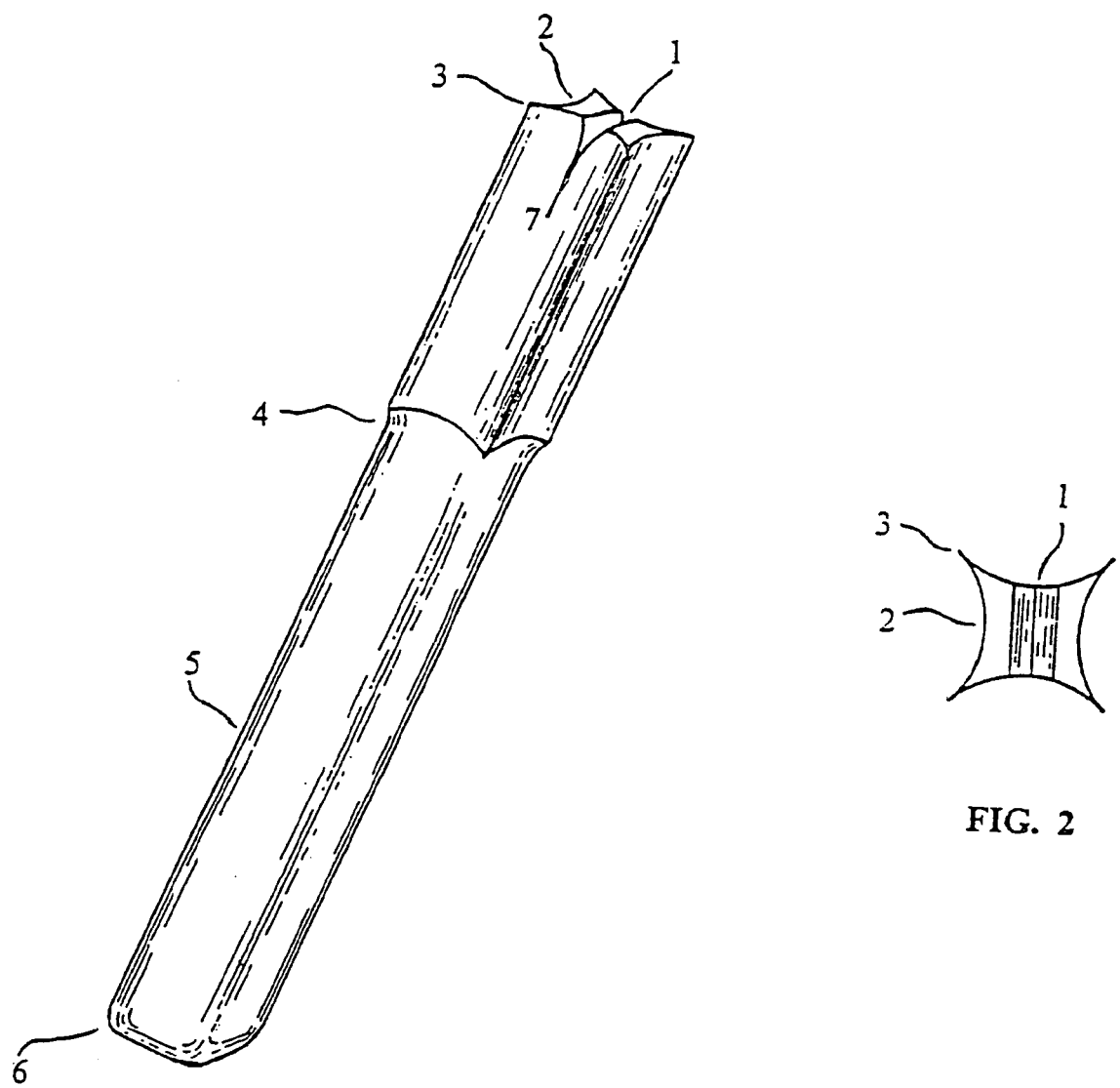
FIG. 1 is a perspective view of one embodiment of a rotational dental floss take up member. The edges are raised with indentations between the edges. The bottom portion of the take up member is rounded for comfort.
FIG. 2 is a top view of the rotational dental floss take up member showing the raised edges and indentation between the edges.
Figure 3:
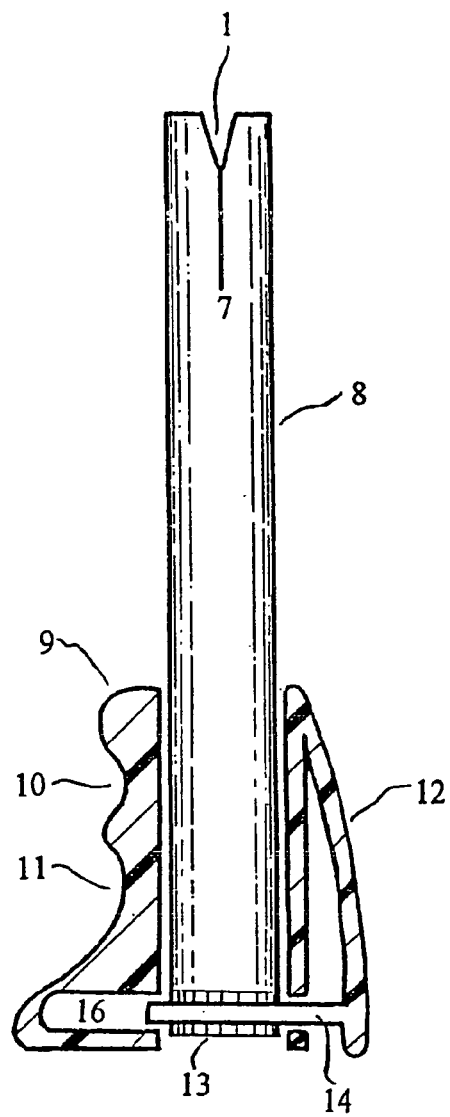
FIG. 3 is a side view of one of the take-up spools which is rotated in a housing. The rotation is accomplished by pressing and releasing a handle on the housing.

One embodiment of the take up spool member is shown in FIG. 1 of the drawings and includes a take-up spool member with major changes to its structure and function over those shown in the take-up spool shown in FIG. 3 of U.S. Pat. No. 5,680,875. In FIG. 1 the notch 1 is gradually tapered down towards the slit 7. This tapering allows the floss to more easily be loaded into the take-up spool member. The paddle wheel-like shape as viewed in FIG. 2 which is formed by protrusion 3 and indentation 2, allows the take-up spool to more easily be rotated by the thumb and fingers of the user. This take up spool member is used like all of the previously disclosed take up spool members. It is not to be inserted inside the mouth during use. Instead the fingers are used inside the mouth and the used or soiled floss is rolled on to the take up spool as fresh segments of floss are needed for flossing.

Sufficient surface texturing on the surfaces of the take up spool member would also provide the user with greater control and grip in rotating and holding the take-up spool member. The lower section 5 of the take-up spool member is rounded allowing for greater comfort while the user is just holding the take-up spool member as he works the floss in between the teeth. The end portion 6 of the take-up spool is also rounded allowing for greater comfort when the floss is loaded into the notch 1 and slit 7 of the take-up spool member. During loading the force is in a downward direction. The user's palm can be more comfortably held under a sufficiently rounded end portion 6 to counteract this downward force.

The transition section 4, is where the cross-section changes from the rounded lower portion 5 to the portion which has paddle wheel-like shape, or texturing, or multiple sided with some type edging or indentation, or any combination of these approaches. The lower section 5 can be tapered with the narrow cross-section being at end portion 6 and the wider cross-section being at transition section 4. The purpose of this tapering is to allow the take-up spool member to be stored between uses in a standard toothbrush holder. One of the most common of these toothbrush holders has one large hole for storing a bathroom drinking cup surrounded by several smaller holes. These smaller holes being large enough to accept the handle of a toothbrush yet small enough to restrict the passage of the bristled portion of the toothbrush, thus holding the toothbrush when it is placed therein.

Although FIG. 2 shows a take up spool member with sharp edges, the protrusions could be more rounded or even rise to a ridge with two squared edges, instead of the single rise to a pointed edge as shown. The transition section 4 could also be manufactured to act as a stop so that the take-up spool can be stored in a standard toothbrush holder. Also a simple protruding ring can be placed anywhere along the lower portion 5 to act as a stop.

Figure 4:
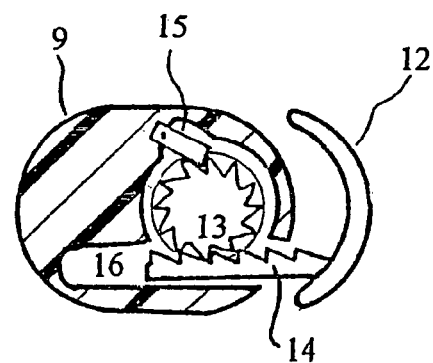
FIG. 4 is a cross sectional cut away view of the housing which illustrates how the pressing and releasing of the handle and a connected geared rack can turn a gear at the bottom of the take up spool member.

The take-up spool in FIG. 3 and FIG. 4 was designed to take advantage of the natural closing and opening motion of the human hand. Moving the hand back and forth from a more open handed position to a more closed handed position requires a lot less dexterity and thought than some of the other hand and finger motions required by some floss tools. The take-up device shown in FIGS. 3 and 4 is comprised of a floss holding element, in FIG. 3 shown as being a notch 1 and slit 7 (a knob like element as shown is FIG. 19A of U.S. Pat. No. 5,680,875 could also be used for securing floss), a rotating advancement element 8 and a hand held housing 9.

In this embodiment handle 12 is moved back and forth by moving the hand back and forth between a more open position and a more closed position. Handle 12 is attached to a toothed rack 14 which engages rotating advancement element gear 13. The open and closing motion of the hand causes rotating advancement element gear 13 to turn, advancing the dental floss on to rotating advancement element 8. This natural opening and closing motion of the hand does not require any dextrous motion of the hand or individual finger or fingers.

Finger indentation 10 and 11 are designed to provide a more comfortable grip for the user. Ratchet locking element 15 prevents rotating advancement element gear 13 from turning in a direction which would cause the floss to unwind off of the rotating advancement element 8. Cavity 16 accepts toothed rack 14 when handle 12 is pressed inward.

Hand held housing 9 could be extended upward to cover almost the entire length of rotating advancement element 8. Also, several different mechanisms besides a tooth rack and ratchet could be used to convert the closing and opening hand motion to the motion of the rotating advancement element. For example, a simple friction mechanism also could be used or a pulley and cord mechanism.

Figure 5:
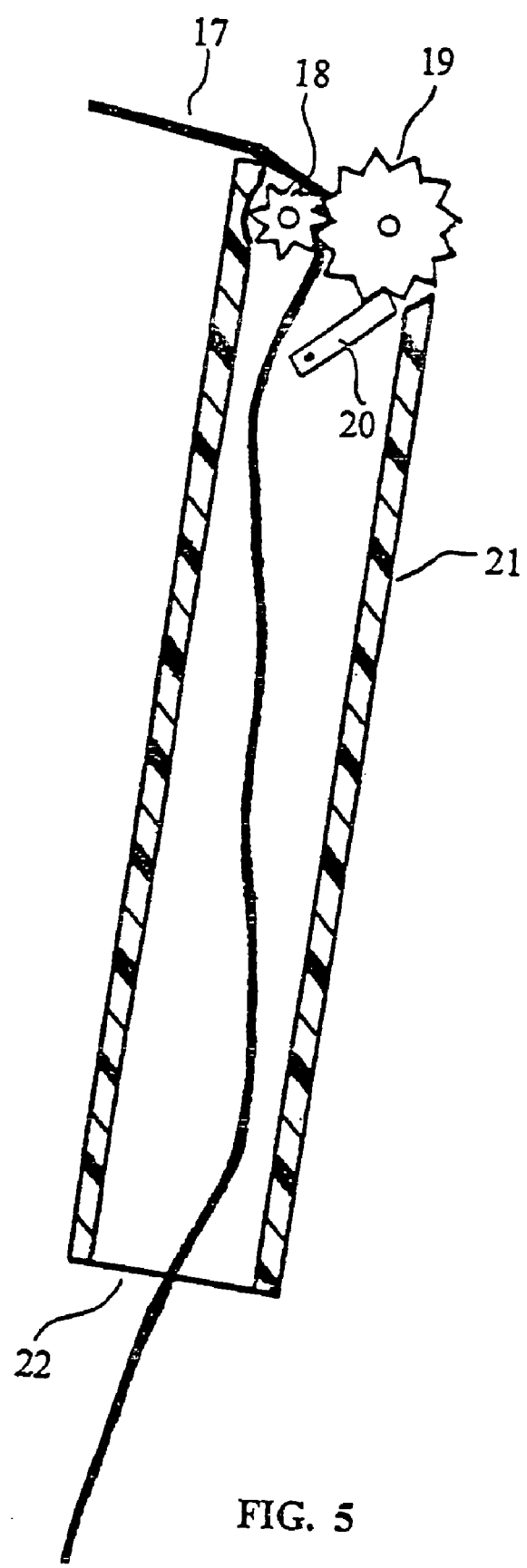
FIG. 5 depicts another embodiment of a dental floss take up member where used floss is rolled past a gear or spool which can be turned directly by the thumb or a finger.

FIG. 5 shows a take-up member which utilizes a different technique for advancing dental floss. The dental floss 17 is drawn in between rotational advancing element 18 and rotational advancing element 19. Rotational advancing element 19 can be rotated with the thumb or it could be placed so that a finger or fingers could be used to rotate it. Turning rotational advancing element 19 with a thumb or finger advances dental floss 17. Both or one of rotational advancing elements 19 and 18 could also be an untoothed wheel or roller. The important principle of this embodiment being that a thumb or finger can be used to directly turn a rotating element which will advance the dental floss.

In this embodiment, the used dental floss is advanced relative to the hand held member 21. Dental floss 17 can exit anywhere on the assembly. In FIG. 5 the dental floss is shown exiting at hole 22 at the bottom of hand held member 21. Hand held member 21 could also be non-hollow. In the non-hollow case, the floss would exit the device after passing between the rotational advancing elements 19 and 18. A ratchet locking element 20 prevents the used floss from be pulled back through the assembly in the wrong direction. The floss can also be advanced by pulling the used floss after it has exited the hollow bodied holding element 21 or after it had passed between rotational advancing elements 18 and 19. After the user has finished flossing, the floss could be removed from assembly by pulling all of the used floss out of hole 22.

In this embodiment the function of the rotational advancing elements 18 and 19 could be performed by other one directional advancement mechanisms such as one or a series of uni-directional valves similar those found in the human heart.

If a single roller were used the floss could be rolled on to it as it was used. The ratchet would keep it from unraveling. Then the ratchet lock could be released when flossing was completed and the floss could be pulled off the roller by allowing this roller to now spin in the opposite direction.

Figure 6:
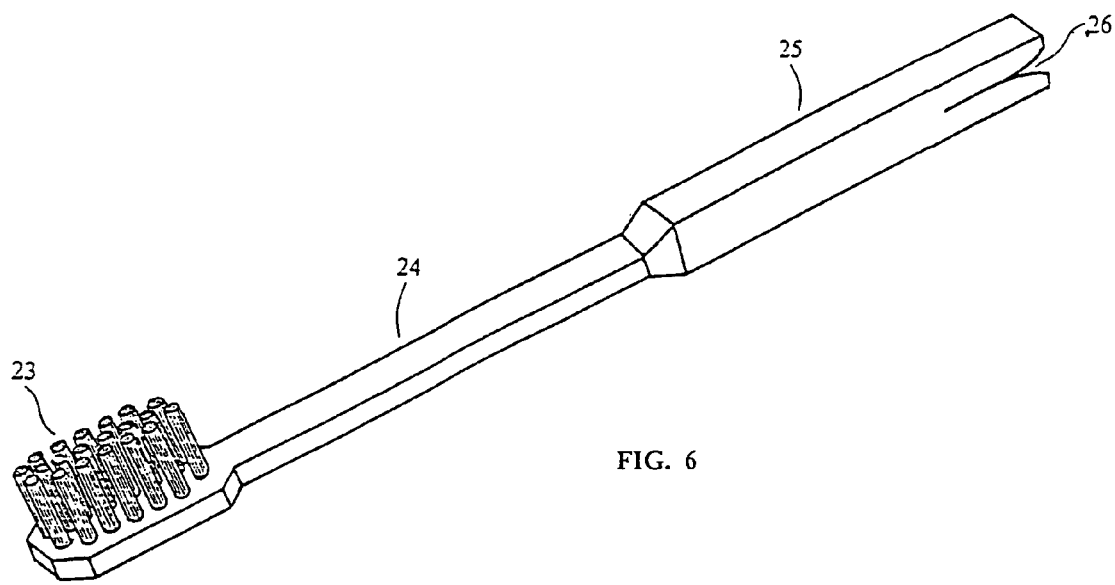
FIG. 6 shows a take up spool member which has been incorporated into the handle of a toothbrush. The dental floss is attached by means of a notch.

FIG. 6 shows the take-up spool element 25 attached to the end opposite the bristled end 23 of a toothbrush 24. The take-up spool portion could have flat sides as disclosed in U.S. Pat. Nos. 5,573,022 and 5,680,875, or it could have a paddle wheel-like design, or the textured surface or pronounced edges, or indentations, or any combination of these approaches. The tapering of notch 26 is also applicable to all take-up spool and toothbrush combination.

The portion of take-up spool element 25 by or around notch 26 could be rounded so that the toothbrush could be stored in a standard toothbrush holder and rounding would also make take up spool element 25 more comfortable to hold during brushing and flossing.

Figure 7:
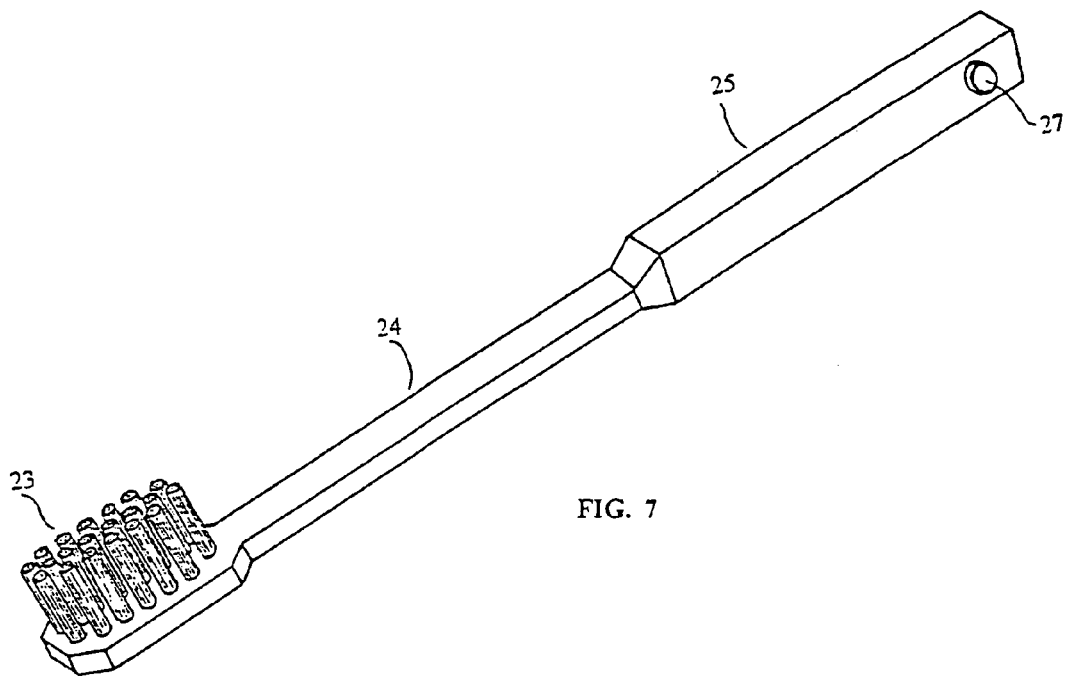
FIG. 7 shows a take up spool member which has been incorporated into the handle of a toothbrush. The dental floss is attached by means of a knob around which the dental floss is wrapped.

FIG. 7 also shows a toothbrush 24 with a take-up spool element 25 at the end opposite the bristle end 23. Instead of a notch being used as the dental floss securing means, a protruding connecting element 27 which as a sufficiently narrow and short neck and a larger head is utilized. The floss is wrapped around the neck portion of the connecting element 27 to secure the floss. As previously described in regards to embodiments in FIGS. 1 and 2, the paddle wheel-like shaping, or textured surfacing and rounding or reshaping of any portion of the handle for comfort and effectiveness during flossing can still be done in this embodiment. However, considerations will also made for how reshaping and texturing affect the comfort and effectiveness of the handle during brushing.

All of the embodiments of take-up spool shown in FIGS. 3, 4, and 5 could be motorized. In FIGS. 3 and 4 the hand held housing could have a small electric motor in it instead of a toothed rack and ratchet. The motor could be activated and de-activated by squeezing and relaxing the hand or by a finger or fingers. In FIG. 5 the motor to be attached directly or indirectly to one or more of the rotational advancing elements 18 and 19 and activated and de-activated in a similar manner.

Figure 8:
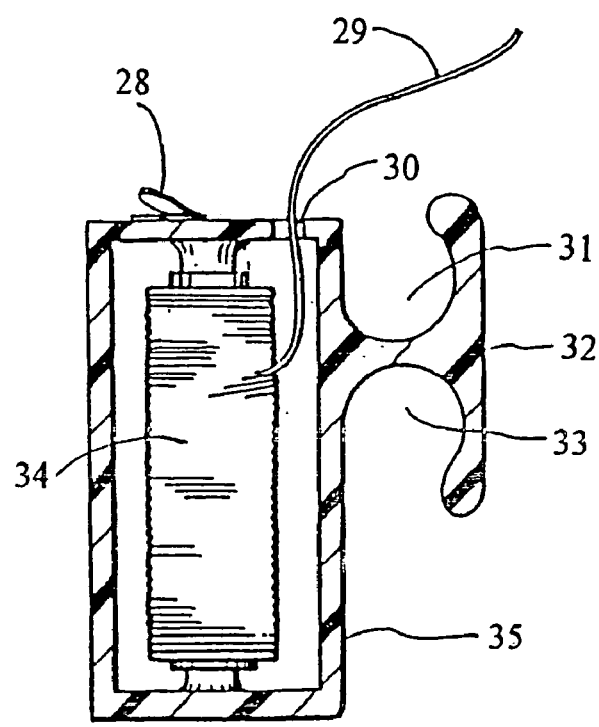
FIG. 8 shows a cutaway view of an embodiment of a dental floss dispenser with a freely rotating spool of the floss. The dispenser has a connected element which can be securely gripped by one or more of the middle to lower fingers of the hand during flossing.
Figure 9:
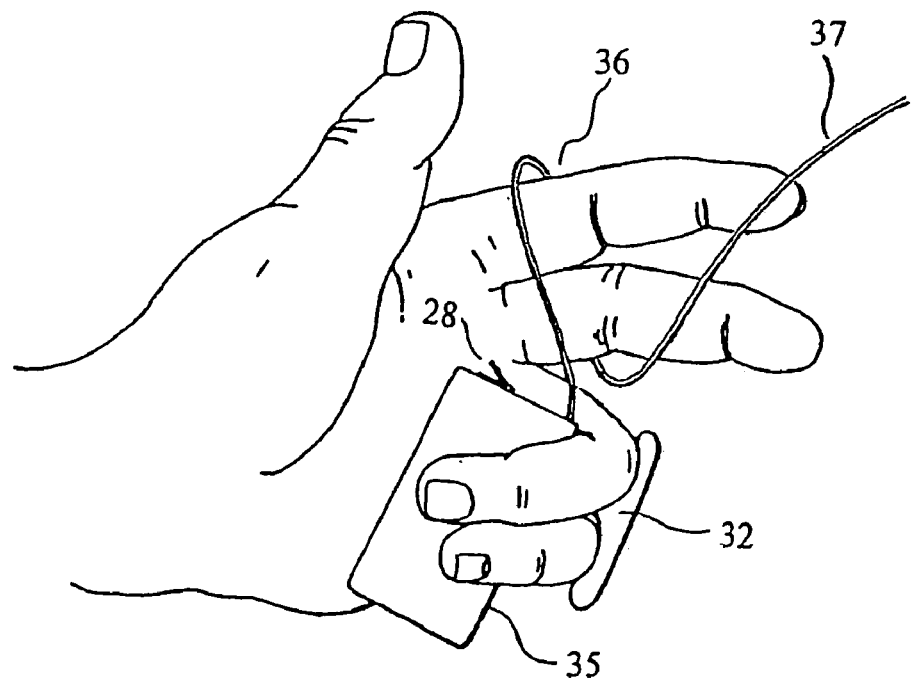
FIG. 9 shows a non-cutaway view of the dispenser of FIG. 8 being held in the hand of a user. The dental floss is shown as being wrapped around a few fingers, this method of wrapping being one of many possible methods which can be used to provide a braking action for the floss during flossing.

FIG. 8 and FIG. 9 show a floss dispensing device which is similar in appearance to FIG. 12 of U.S. Pat. No. 5,680,875 but it is very different in function. This device is simpler to manufacture because this device does not have a locking mechanism like the device in U.S. Pat. No. 5,680,875. The floss dispenser shown in FIG. makes it possible for the user to use only the amount of dental floss which is required during the flossing session. The user does not have to guess at the amount of floss which will be needed and then remove and cut this length from this floss dispenser. Instead the user secures a dispenser 35 by inserting a finger or fingers in one or both finger hole 31 and finger hole 33 of a finger holding element 32. The dispenser is designed so that the user has full use of his upper fingers and thumb which can be used for manipulating the floss in between the user's teeth.

Sufficient floss 29 to begin the flossing process is removed from a floss spool 34 inside dispenser 35 through hole 30. To secure the floss during actual use, the floss 37 can be wrapped around any finger or fingers. One potential wrapping is shown at point 36 in FIG. 9. There are numerous wrapping methods and techniques for securing the floss. Some users may be able to hold the floss sufficiently secure without wrapping around any fingers, simply by pinching the floss between their thumb and index finger.

The great advantage of this dispenser is that it allows the user to use only the amount of floss which is needed. The user does not cut the floss free of the dispenser until flossing is completed. When the user is finished flossing, the floss is cut using cutter 28.

Figure 10:
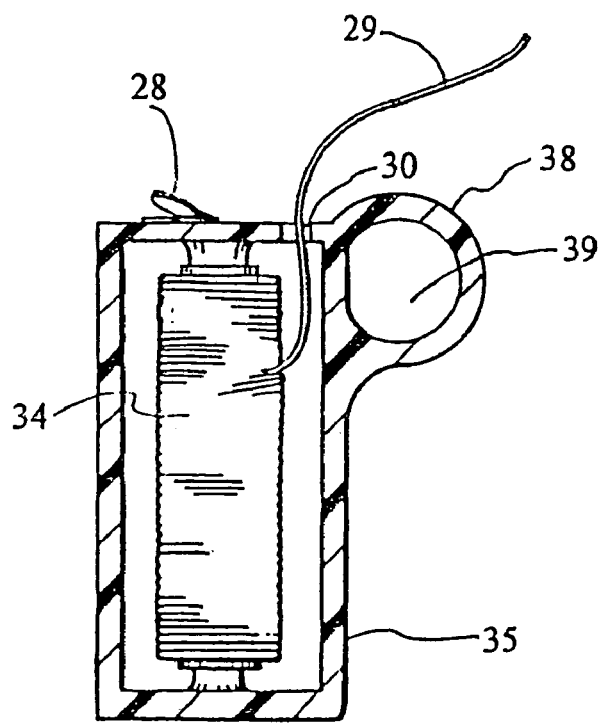
FIG. 10 shows a cutaway view of an embodiment of a dental floss dispenser with a freely rotating spool of the floss. The dispenser has a connected ring like element which can be securely gripped by a lower or middle finger of the hand during flossing.
Figure 11:
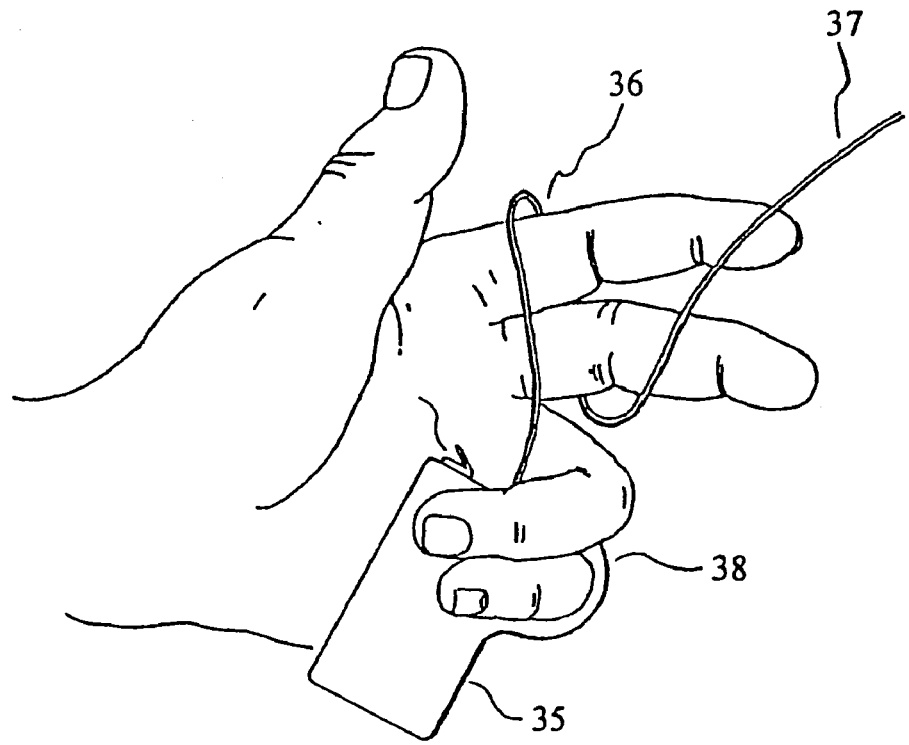
FIG. 11 shows a non-cutaway view of the dispenser of FIG. 10 being held in the hand of a user. The dental floss is shown as being wrapped around a few fingers, this method of wrapping being one of many possible methods which can be used to provide a braking action for the floss during flossing.

FIG. 10 and FIG. 11 show a device similar to the device shown in FIG. 8 and FIG. 9. The difference is the finger holding device is a finger ring 38 which completely encircles finger hole 39. The floss is dispensed and held as shown in FIG. 11 with the floss being wrapping around fingers or finger at point 36 or at any other point or points where the user may choose to wrap the floss strand 37. Again, some users may be able to hold the floss sufficiently secure, without wrapping around any fingers, simply by pinching the floss with their fingers. Also, the devices shown in FIGS. 8 through 11 instead of being held by the fingers could be designed to clip to the hand.

FIGS. 12, 13, and 14 disclose a device which is held like a sewing thimble. It is different than the device shown is FIGS. 6A, 6B, 7, 8A, 8B, 9A and 9B of U.S. Pat. No. 5,680,875 because that device is worn like a ring around the user's finger. Because the device of FIGS. 12, 13 and 14 is placed on the tip of the finger it requires less time to place in position and it is easier to design a size that will comfortably fit a larger number of different sizes and shapes of fingers. The floss 45 is stored on a spool 41 which is enclosed by a sleeve 46. The exposed portion of the spool may or may not have a wavy pattern 40 for providing added gripping ability when the sleeve bottom 47 is held firmly against the palm of the user's hand. The floss strand 44 exits the sleeve 46 through a hole 42. A floss cutter 43 is attached to the sleeve to cut off the floss after it is used. This cutter 43 can be recessed in a protective trough or have some other protection built around it. The floss 49 can be wrapped around a finger or fingers 48 as shown in FIG. 14 to provide added gripping ability.

Also the floss spool can be completely internal to the sleeve, with no exposed surfaces. In this case sufficient grip could be provided just by wrapping the floss around a finger or fingers, similar to the concept shown in FIGS. 8, 9, 10, and 11 or by pinching the floss between the thumb and a finger.

Figure 15:
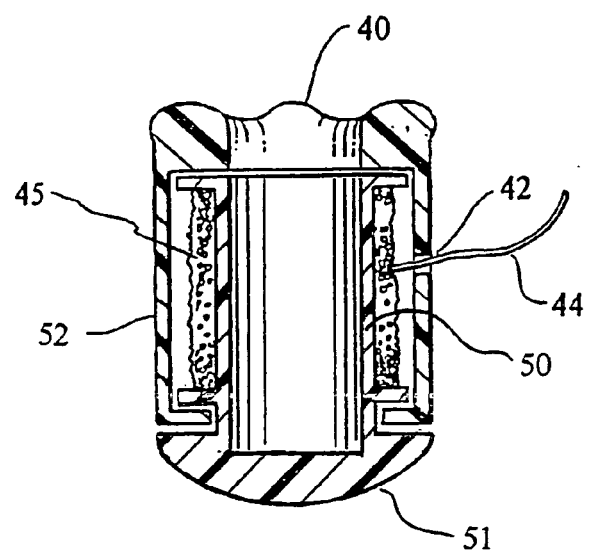
FIG. 15 shows a cutaway view of another embodiment of a dental floss dispenser with a freely rotating sleeve covering the floss. The spool rotates on the finger while the sleeve is held in place by the taut strand of floss which extrudes from the hole. The base of the dispenser is connected to the spool to create a braking action on the spool when the user presses the dispenser into the palm of the hand.
Figure 16:
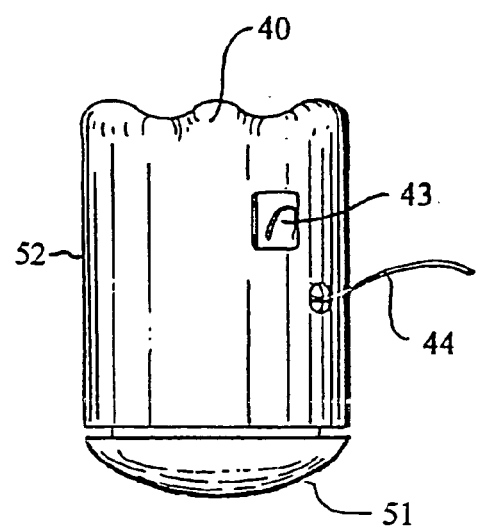
FIG. 16 shows a non-cutaway view of the dispenser of FIG. 15 having a freely rotating sleeve and a spool which is connected to the base of the dispenser.
Figure 17:
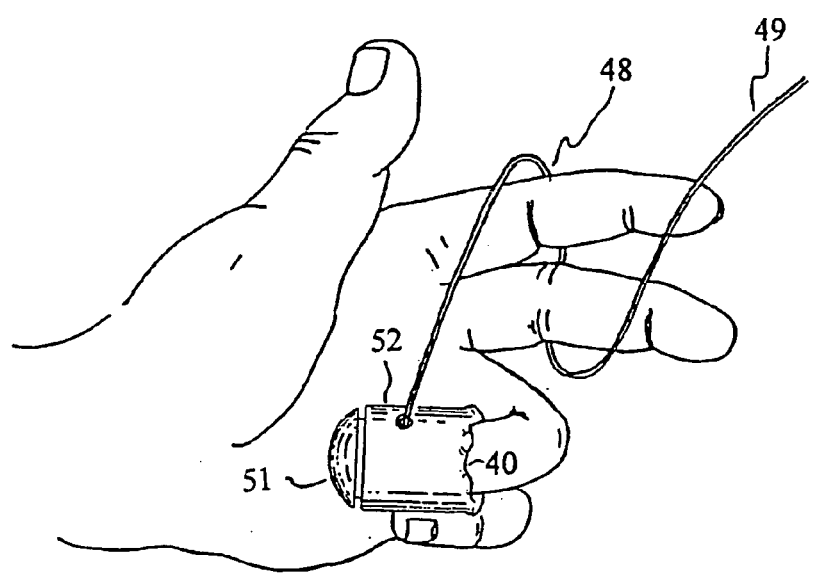
FIG. 17 shows a non-cutaway view of the dispenser of FIG. 15 on the finger tip of a user. Pressing the spool into the palm of the hand or wrapping the floss strand around available fingers are some of methods which can be used to tension the floss strand during flossing.

The device shown in FIGS. 15, 16 and 17 is similar to the device shown in FIGS. 12, 13 and 14. However, the base of the device is a spool bottom 51. It is not the sleeve bottom 47 as shown in FIGS. 12, 13 and 14.

The floss 45 is stored on a spool 50 which is partially enclosed by a sleeve 52. The sleeve 52 is connected to top of the device where the finger is inserted in finger hole 40. The floss strand 44 exits the sleeve 52 through a hole 42.

A floss cutter 43 is attached to the sleeve to cut off the floss after it is used. This cutter 43 can be recessed in a protective trough or have some other protection built around it. The spool 50 is restrained from rotating by pressing the spool bottom 51 into the palm of the hand as shown in FIG. 17. The floss 49 can be wrapped around a finger or fingers 48 as shown in FIG. 17 to provide added gripping ability.

Figure 18:
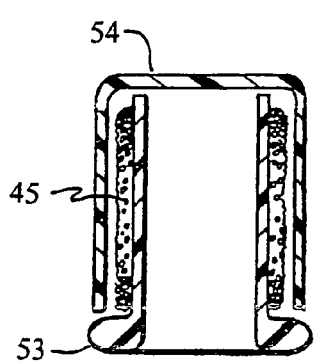
FIG. 18 shows a cutaway view of another embodiment of a dental floss dispenser. The spool of dental floss has a removal and replaceable protective covering.
Figure 19:
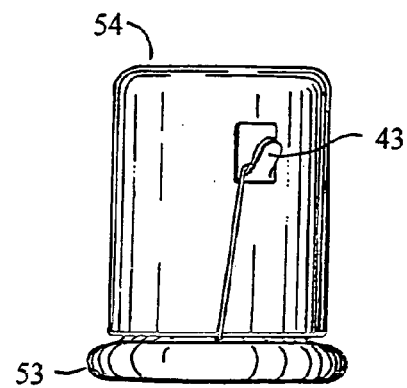
FIG. 19 shows a non-cutaway view of the dispenser of FIG. 18 having a removable and replaceable covering and a floss cutter element on said covering.
Figure 20:
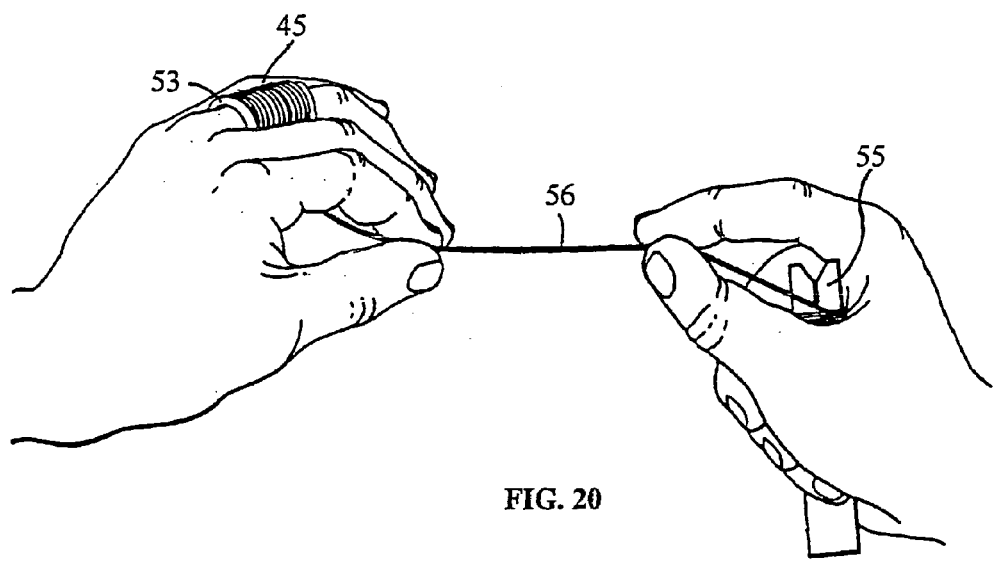
FIG. 20 shows a non-cutaway view of the dispenser of FIG. 18 on the finger of a user. Bending the finger restrains the rotating of the spool providing the needed tension for flossing. As with all floss dispenser, the spool can be used with or without a take up spool member being held in the other hand.
Figure 21:
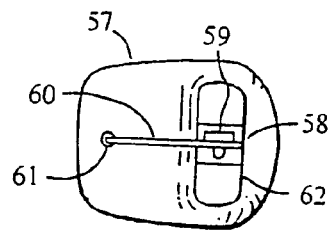
FIG. 21 is a top view of yet another embodiment of an enhanced dental floss dispenser having a contoured body for easy gripping, a deep indentation in the top thereof for easy access to the dental floss, and a recessed floss cutting tool to prevent any injuries to the user.
Figure 22:
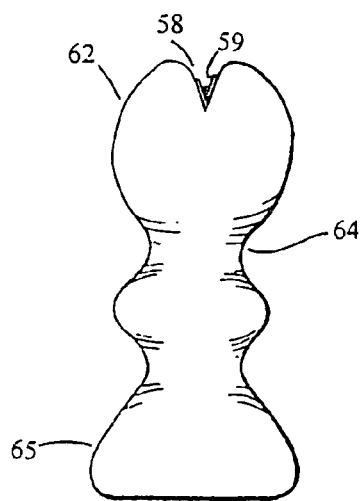
FIG. 22 is a front view of the dental floss dispenser of FIG. 21 showing the contoured body and the recessed floss cutter.
Figure 23:
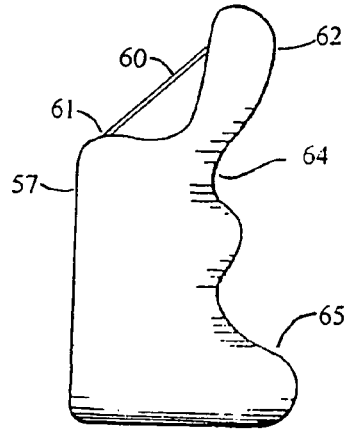
FIG. 23 is a side view of the dental floss dispenser of FIG. 21 showing the body contours and a deep indentation in the top thereof for easy access to the dental floss.
Figure 24:
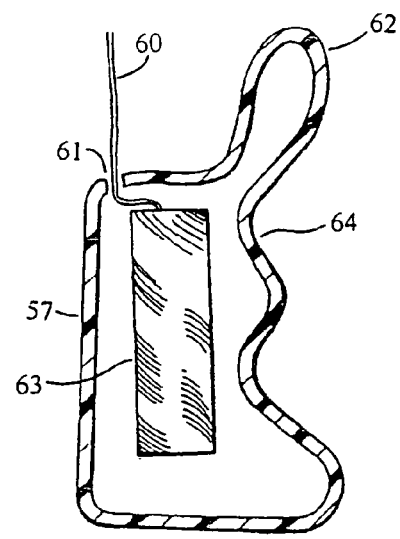
FIG. 24 is a side cut-away view of the dental floss dispenser of FIG. 21 showing the internal spool of dental floss.
Figure 25:
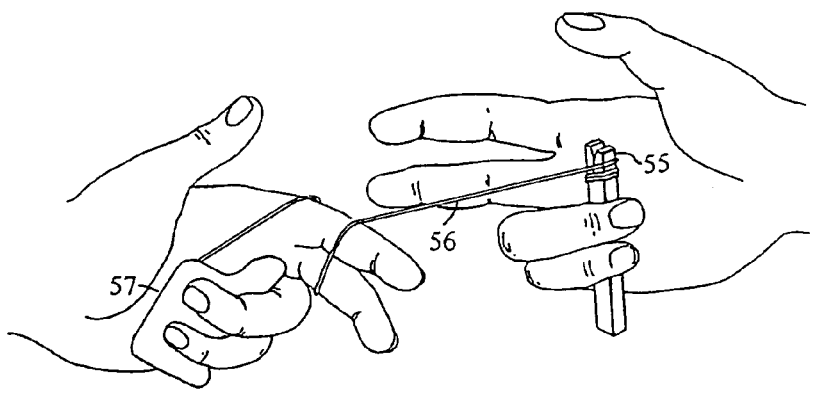
FIG. 25 shows a non-cutaway view of the dispenser of FIG. 21 being held in the hand of a user. The dental floss is shown as being wrapped around a few fingers, this method of wrapping being one of many possible methods which can be used to provide a braking and tensioning action for the floss during flossing. As with all floss dispensers, the dispenser can be used with or without a take up spool member being held in the other hand.

A finger spool 53 shown in FIGS. 18, 19 and 20 has a removable covering 54. The removable covering 54 helps keep the unused floss clean between uses. To use, the removable covering 54 is removed and the finger spool 53 is place on the finger tip or the finger of the user. Bending the finger restrains the rotation of the finger spool and provides tensioning of the floss strand 56 for proper use. The removable covering 54 has an attached floss cutter 43 so the floss strand 56 can be cut after flossing is completed. The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

Figure 26:
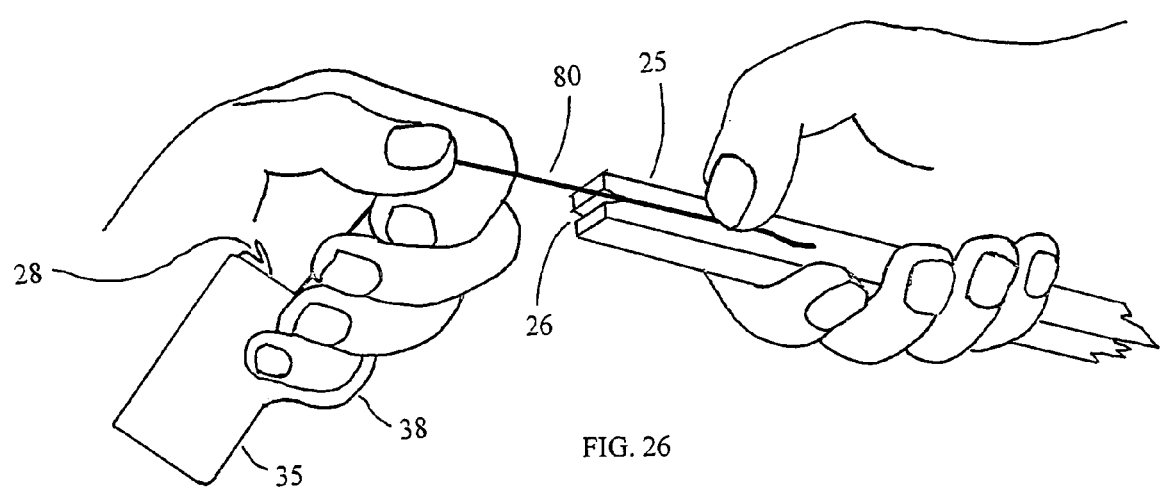
FIG. 26 shows the beginning position for loading the floss into the take-up spool member by holding the floss against the side of the take-up spool member.

As show in FIG. 26 to load floss 80 into take-up spool member 25, a length of floss 80 is removed from dispenser 35 and then held against the side of take-up spool member 25.

Figure 27:
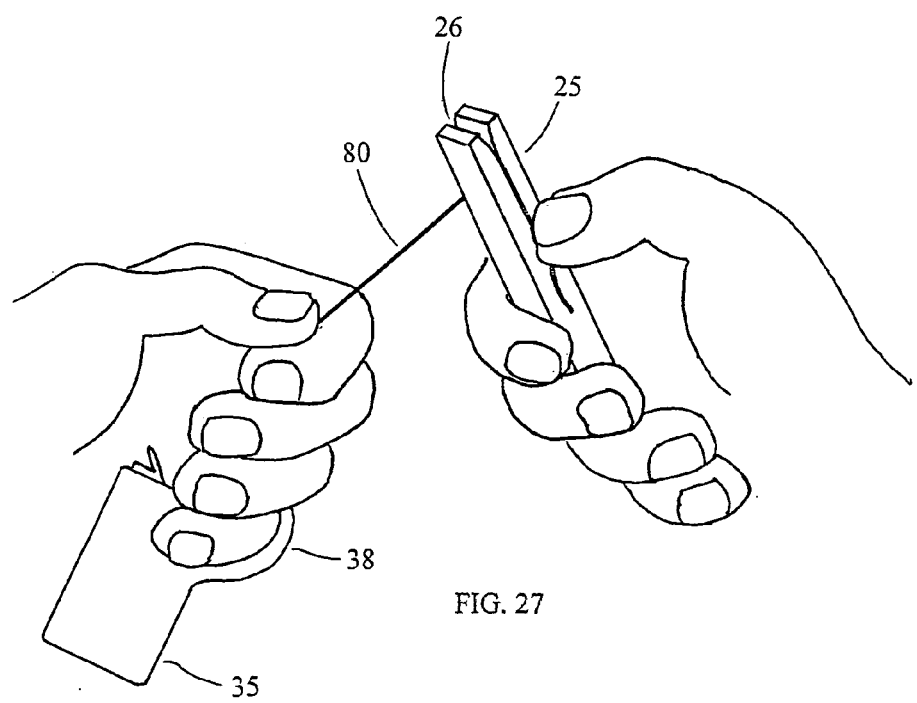
FIG. 27 shows the completion of the loading of the floss into the take-up spool member by turning the take-up spool member and causing the floss to be pulled down into the notch.

Floss 80 is securely loaded into take-up spool member 25 as shown in FIG. 27 by turning take-up spool member 25 up and away from dispenser 35 and thus causing floss 80 to be securely pulled into notch 25.

Figure 28:
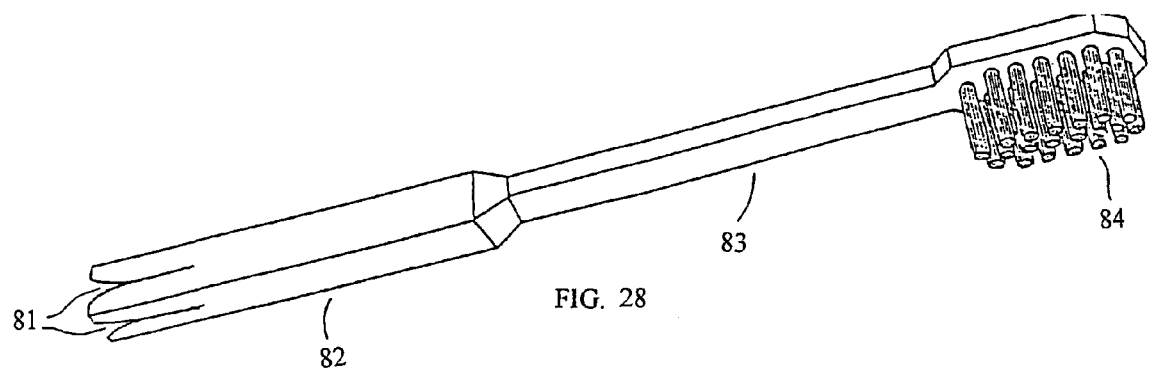
FIG. 28 shows a take-up spool member which is part of a toothbrush handle. The take-up spool having double notches for ease of loading and assuring in case one notch loses its gripping ability another notch will be available.

Through frequently use, notch 25 as shown in FIG. 27 and FIG. 28 can lose its ability to firmly securely floss 80. FIG. 28 shows a take-up spool member 28 as part of a toothbrush handle 83 with bristles 84 on the opposite end. The take-up spool having double notches 81 assuring in case one notch loses its gripping ability another notch will be available. Also because one of the double notches 81 will always be correctly oriented with floss 80, double notches 81 makes it possible for the user of take-up spool member 28 to load floss 80 in all possible the orientation of the floss 80 to the end of the take-up spool member 28 and thus load floss 81 with greater ease.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

The invention claimed is:

1. A dental floss holding and collecting device comprising a toothbrush handle having a substantially straight end portion adapted to be held by a user of the device and having an end and a main axis, said toothbrush handle having a plurality of tapered notches extending from the end into the end portion, each tapered notch having an associated holding slot, each tapered notch being configured for guiding a previously unattached end portion of a length of dental floss into the associated holding slot and securing the dental floss therein to facilitate a flossing process by securely holding and manipulating one end of the length of dental floss in a selected holding slot during the flossing process and presenting a portion of the length of dental floss for use between two teeth during the flossing process, each tapered notch and associated slot extending into the handle portion along the main axis and being positioned on the toothbrush handle so that rotation of the toothbrush handle with the end of the length of dental floss secured therein will wind dental floss onto the handle to advance the dental floss to present a new portion of the length of dental floss for use between the two teeth at desired times during the flossing process.

2. A dental floss holding and collecting device according to claim 1, wherein the plurality of tapered notches and associated holding slots are two intersecting tapered notched and associated holding slots arranged perpendicularly to one another.

3. A dental floss holding and collecting device according to claim 2, wherein the end portion of the toothbrush handle has a width, and wherein the tapered notches and associated holding slots each have a width extending across the width of the handle and intersecting one another centrally of the width of each tapered notch and associated slot.

4. A dental floss holding and collecting device according to claim 3, in combination with a dispenser of dental floss, said dispenser of dental floss comprising:
   (a) a supply of dental floss within said dispenser; and
   (b) a dispenser body shaped to fit substantially matingly in a user's hand so that said dispenser can be sufficiently secured by one or more middle to lower fingers of the hand leaving one or more upper fingers of the hand free to maneuver the dental floss within the user's mouth.

5. A dental floss holding and collecting device according to claim 4, wherein the toothbrush handle is configured to be easily gripped and rotated for advancing dental floss onto the handle as said dental floss is used.

6. A dental floss holding and collecting device according to claim 5, wherein the handle has opposite ends with bristles positioned at one opposite end and the tapered notches and associated holding slots positioned at the other opposite end.

7. A dental floss holding and collecting device according to claim 1, in combination with a dispenser of dental floss, said dispenser of dental floss comprising: (a) a dispenser body; (b) a supply of dental floss within said dispenser; (c) a protruding element for substantially securing said dispenser during cleaning of the user's teeth by one or more middle to lower fingers of the hand thus leaving one or more upper fingers of the hand free to maneuver the dental floss within the user's mouth and (d) said dispenser body shaped to fit substantially matingly in the user's hand so that said dispenser can be securely and comfortably held during the flossing process.

8. A dental floss holding and collecting device according to claim 1, in combination with a dispenser of dental floss, said dispenser of dental floss comprising: (a) a protruding element for substantially securing said dispenser during cleaning of the user's teeth by one or more middle to lower fingers of the hand thus leaving one or more upper fingers of the hand free to maneuver the dental floss within the user's mouth; and (b) a supply of dental floss within said dispenser.

9. A dental floss holding and collecting device according to claim 1, in combination with a dispenser of dental floss, said dispenser of dental floss comprising: (a) a spool wound with dental floss; (b) a sleeve around said spool which is rotatable relative to said spool; (c) a hollow portion in said dispenser, in said sleeve and in said spool large enough for the user's finger tip to be inserted into said hollow portion; and (d) a hole in said sleeve through which dental floss is dispensed.

10. A dental floss holding and collecting device according to claim 1, in combination with a dispenser of dental floss, said dispenser of dental floss comprising: (a) a spool wound with dental floss; (b) a removable and replaceable covering for said spool; and (c) a hollow portion in said spool large enough for the user's finger or finger tip to be inserted into said hollow portion.

11. A dental floss holding and collecting device according to claim 1, in combination with a dispenser of dental floss, said dispenser of dental floss comprising: (a) a supply of dental floss within said dispenser; (b) a dispenser body shaped to fit substantially matingly in the user's hand so that said dispenser can be sufficiently secured by one or more middle to lower fingers of the hand leaving one or more upper fingers of the hand free to maneuver the dental floss within the user's mouth; and (c) a cutting element for the dental floss positioned with respect to the dispenser body such that it is not possible for the user to contact the cutting element in such a way which would result in harm or injury to said user.

12. A method of using dental floss to floss teeth of a user, comprising:
   obtaining a dispenser of dental floss, comprising: (a) a dispenser body; (b) a supply of dental floss within said dispenser body; (c) an outlet through the dispenser body for allowing the user to pull dental floss from the supply of dental floss in the body; (d) a protruding element for substantially securing said dispenser during cleaning of the user's teeth by one or more middle to lower fingers of the hand thus leaving one or more upper digits of the hand free to hold and maneuver the dental floss within the user's mouth and (e) said dispenser body shaped to fit substantially matingly in the user's hand so that said dispenser can be securely and comfortably held during the flossing process;
   wrapping the dental floss as it comes from the dispenser around the first two fingers of the user's hand holding the dispenser and leaving a length of dental floss with a free end extending from the hand;
   holding the free end; and
   flossing the user's teeth with the dental floss.

13. A method of using dental floss to floss teeth of a user according to claim 12, wherein the protruding element extends from the body and includes an opening positioned to receive a user's finger therethrough when the dispenser is held in a user's hand.

14. A method of using dental floss to floss teeth of a user according to claim 13, wherein the protruding element is positioned to receive the user's little finger through the opening.

15. A method of using dental floss to floss teeth of a user according to claim 12, wherein the protruding element is a T-shaped element having a leg portion extending from the body positioned so that the leg portion of the T-shaped element fits between two fingers of the user's hand when the dispenser is held in a user's hand.

16. A method of using dental floss to floss teeth of a user according to claim 12, wherein the protruding element is a projection from the body positioned to fit at least partially between two fingers of the user's hand when the dispenser is held in a user's hand.

17. A method of using dental floss to floss teeth of a user according to claim 12, additionally including a cutting element for the dental floss positioned in the dispenser whereby the dispenser is shaped around said cutting element such that it is not possible for the user to contact the cutting element in such a way which would result in any harm or injury to said user.

* * * * *